United States Patent [19]

Goode et al.

[11] Patent Number: 5,013,310

[45] Date of Patent: * May 7, 1991

[54] METHOD AND APPARATUS FOR REMOVING AN IMPLANTED PACEMAKER LEAD

[75] Inventors: Louis Goode, Evans City; Frederick J. Shipko, Spring Church, both of Pa.

[73] Assignee: Cook Pacemaker Corporation, Leechburg, Pa.

[*] Notice: The portion of the term of this patent subsequent to Jan. 29, 2008 has been disclaimed.

[21] Appl. No.: 298,100

[22] Filed: Jan. 17, 1989

Related U.S. Application Data

[63] Continuation-in-part of Ser. No. 269,771, Nov. 9, 1988.

[51] Int. Cl.$^5$ .............................................. A61B 17/00
[52] U.S. Cl. ......................................... 606/1; 128/785
[58] Field of Search .............................. 128/783-786, 128/642, 419 P, 328 V, 303 R; 606/127, 128, 1

[56] References Cited

U.S. PATENT DOCUMENTS

| | | | |
|---|---|---|---|
| 3,243,755 | 3/1966 | Johnston | 439/841 |
| 3,841,308 | 10/1974 | Tate | 128/772 |
| 4,471,777 | 9/1984 | McCorkle | 128/303 R |
| 4,541,681 | 9/1985 | Dorman et al. | 339/100 |
| 4,574,800 | 3/1986 | Peers-Trevarton | 128/785 |
| 4,576,162 | 3/1986 | McCorkle | 128/303 R |
| 4,582,056 | 4/1986 | McCorkle | 128/303 R |
| 4,706,671 | 11/1987 | Weinrib | 604/104 |
| 4,762,130 | 8/1988 | Fogarty et al. | 604/96 |
| 4,791,939 | 12/1988 | Maillard | 128/419 P |
| 4,834,090 | 5/1989 | Moore | 128/303 R |
| 4,848,342 | 7/1989 | Kaltenbach | 604/104 |

FOREIGN PATENT DOCUMENTS

| | | | |
|---|---|---|---|
| 2558376 | 7/1985 | France | 128/785 |

OTHER PUBLICATIONS

"Pacemaker Electrode Explantation Set," William Cook Europe A/S, date unknown.

Meibom, "A New Method for Transvenous Lead Explantation," 3rd European Symposium on Cardiac Pacing, Torremolinos, Malaga, Spain, *PACE*, vol. 8, May-Jun. 1985, Part II, Abstract 215, p. A-54.
Meibom et al., "A New Method for Removal of Embedded Endocardial Electrodes," First Asian-Pacific Symposium, *PACE*, vol. 3, May-Jun. 1980, Abstract No. 77, p. 380.

(List continued on next page.)

*Primary Examiner*—Kyle L. Howell
*Assistant Examiner*—Kennedy J. Schaetzle
*Attorney, Agent, or Firm*—Richard J. Godlewski

[57] ABSTRACT

Heart lead removal apparatus and method are disclosed for removing a pacemaker lead from a heart through a blood vessel leading thereto. The apparatus comprises a flexible stylet wire with an expandable wire coil attached to the distal end for engaging the coiled structure of the pacemaker lead. A lockable mechanism grasps the proximal end of the lead, and a wire guide is inserted in the passageway of the lead to determine its size and clear any blockage therein. The stylet wire is inserted in the longitudinal passageway of the coiled structure to the distal end of the pacemaker lead. The stylet wire is rotated in a direction to unwind and expand the wire coil and engage the coiled structure, thereby securing the stylet wire to the pacemaker lead. A tie secures the insulating material to the coiled structure of the lead at the proximal end thereof to limit motion and to apply a uniform extraction force to the entire lead. A separator tube is inserted over the proximal end of the stylet wire and the lead and moved along the entire length of the lead to first separate the restricted lead from the blood vessel and then the heart cavity. The separator tube, stylet wire, and pacemaker lead are then removed from the heart cavity and blood vessel without causing any significant injury to the heart cavity wall.

24 Claims, 4 Drawing Sheets

OTHER PUBLICATIONS

"Dotter Intravascular Retriever Set and Components," *Cook ® Diagnostic and Interventional Products for Radiology, Cardiology and Surgery, Intravascular Retrieval*, 1986, p. 3.

"Wilson-Cook Grasping Forceps," *Wilson-Cook Medical, Inc., Products for Gastroenterology, Endoscopy and Surgery*, 1986-87 catalog, p. 41.

"Loop Retrievers," *Cook Urological ®, Urological Surgical Products, Stone Extractors and Retrievers*, 1986, p. 9.

"Boren-McKinney Retriever Set," *Cook Urological ®, Urological Surgical Products, Stone Extractors and Retrievers*, 1986, p. 9.

"Curry Intravascular Retriever Sets and Components," *Cook ® Diagnostic and Interventional Products for Radiology, Cardiology and Surgery, Intravascular Retrieval*, 1986, p. 2.

"Grasping Forceps," *Cook Urological ®, Urological Surgical Products, Stone Extractors and Retrievers*, 1986, p. 8.

METHOD AND APPARATUS FOR REMOVING AN IMPLANTED PACEMAKER LEAD

CROSS-REFERENCE TO RELATED APPLICATION

This application is a continuation-in-part of application Ser. No. 07/269,771, filed Nov. 9, 1988, entitled "Method and Apparatus for Separating a Coiled Structure from Biological Tissue."

TECHNICAL FIELD

This invention relates to electrical, heart pacemaker leads and particularly to method and apparatus for removing a pacemaker lead implanted in a heart.

BACKGROUND OF THE INVENTION

A heart pacemaker is generally implanted subcutaneously in the chest wall along with a lead for conducting electrical signals, such as stimulating pulses, between the pacemaker and the heart. The lead is surgically implanted through a vein leading to a cavity of the heart. A typical heart lead includes one or more spirally coiled wires having a hollow inner passageway that extends the entire length of the coiled wires. The coiled structures are positioned in the lead either coaxially or laterally. The coiled wires are surrounded by an insulating material such as a flexible tube or coating comprising, for example, silicone or polyurethane for insulating the wires from body fluids as well as each other. However, one problem is that, over time, fibrotic tissue commonly encapsulates the heart lead especially in areas where there is low velocity blood flow. When small diameter veins through which the lead passes become completely occluded with fibrotic tissue, separating the lead from the vein is difficult and causes severe damage to or destruction of the vein. Furthermore, the separation is usually not possible without restricting or containing the movement of the heart lead.

In most cases, the useful life of a heart lead lasts for many years. However, should the heart lead become inoperative due to corrosion or other effects of body fluids or should another heart lead be desired, the existing heart lead is typically left in place, and a new heart lead is implanted through another vein. One problem with leaving an implanted heart lead in place, particularly in the heart, is that the lead partially restricts the operation of the various heart valves through which the lead passes. If several leads passing through a heart valve are left in place, the operation of the heart valve and the efficacy of the heart is significantly impaired.

Another problem associated with leaving heart leads in place, particularly in blood vessels, is that an infection may develop around the lead, thereby requiring surgical removal. Surgical removal of the lead from the heart often involves open heart surgery which is complicated, risky, and costly.

One method for transvenous removal of a heart lead involves a prior art heart lead removal tool that utilizes a hollow, rigid tube and a beveled rod tip for engaging and deforming the coiled structure of the heart lead. However, when the heart lead cannot be removed because of some complication, a serious problem is that the tip of the tool is locked in place and cannot be removed from the heart lead. As a result, the tool and heart lead must be surgically removed. Furthermore, the rigid tube of the tool can easily puncture a blood vessel or a heart cavity wall.

Another method is to transvenously extract the heart lead manually without the aid of a tool. Such method is possible only when the lead has not ben encapsulated in a blood vessel. Even then, this method has a number of problems. First, when the polyurethane or silicone insulation surrounding the coiled wire is damaged, the insulation can sever and cause the coiled structure of the lead to unwind and to damage the heart and blood vessels. Secondly, when both the coil structure and insulation are severed in the heart or a blood vessel, surgical removal is required. Thirdly, most heart leads typically include tines or a corkscrew at the tip or a conically shaped tip for securing the distal end of the heart lead to a heart cavity wall. After fibrotic tissue has encapsulated the tip, unaided manual removal of the heart lead tip from the heart cavity wall may cause an inward extension or inversion of the wall, or even worse, permanent damage to the heart such as tearing a hole in the heart cavity wall.

SUMMARY OF THE INVENTION

The foregoing problems are solved and a technical advance is achieved with illustrative apparatus for removing an electrical pacemaker lead implanted in a heart. The apparatus comprises a stylet wire and a wire coil attached about the distal end of the stylet wire. The stylet wire is insertable into the longitudinal passageway of the implanted lead for controlling the movement of the lead. When the stylet wire is inserted in the passageway of the lead, the coil wire is operated for securing the distal end of the stylet wire to the lead.

Normally prior to insertion of the stylet wire, a wire guide is utilized for determining the passageway of the lead for the stylet wire. In one instance, the wire guide is inserted to reopen or unblock an occluded passageway or to detect a damaged or deformed coiled structure. A control mechanism is attached at the proximal end of the wire guide to rotate and move the wire guide through the passageway. Typically smaller in diameter than the stylet wire, the wire guide is used to detect and measure the inside diameter of another coaxially positioned coiled structure that has retracted into or broken off in the passageway of a larger coiled structure. A plurality of wire guides with different size diameters are utilized to determine the actual inside diameter of the coiled structure. This aids in the selection of a stylet wire and wire coil having a combined outside diameter corresponding to the inside diameter of the coiled structure.

The invention also includes apparatus for grasping the pacemaker lead, for example, at the proximal end where the lead may have been previously cut exposing only a short segment extending from the subclavian vein. The grasping apparatus includes a pair of opposing jaws with pliable material affixed thereto for grasping the lead without deforming the coiled structure within the lead. The jaws are connected to pivotly interconnected elongated members that operate the jaws between open and closed positions. The proximal end of the members are connected to a locking mechanism for locking the jaws in a closed position. The pliable material on each jaw includes a channel for grasping the lead and applying pressure thereto in a uniform manner. This apparatus advantageously grasps the lead without deforming the coiled structure while the wire guide and stylet wire are inserted into the passageway of the lead. The grasping apparatus also prevents the coiled structure from retracting into the insulating material as well as preventing the lead from retracting into the vein.

A control mechanism of the lead removal apparatus such as a looped handle formed or attached at the proximal end of the stylet wire controls the movement of the stylet wire. This mechanism is used to rotate the stylet wire in a direction opposite to the direction that the coiled structure is wound for operating the wire coil to engage the coiled structure. When the wire coil and coiled structure are engaged, the stylet wire is, as a result, firmly secured to the heart lead. When secured to the lead, the stylet wire is further rotated by the control mechanism to dislodge the distal end or tip of the lead from the heart tissue. Such a procedure is advantageously suited for a pacemaker lead having an electrode tip that is lodged in the heart tissue with a corkscrew mechanism.

After the stylet wire has been secured to the lead, a tie such as nylon cord or suture material is secured about the proximal end of the lead to limit movement of the coiled structure and the insulating material. With the coiled structure and the insulating material secured at the proximal end, the stylet wire applies force both to the insulating material and the coiled structure during removal of the lead. Otherwise, the stylet wire pulls only on the coiled structure which may break or unravel leaving the insulating material in place and causing possible injury to surrounding tissue. Securing the stylet wire to the lead and the insulating material to the coiled structure advantageously controls and limits the movement of the heart lead and prevents the coiled structure and insulating material from stretching, unraveling, or breaking during subsequent removal and, if necessary, during separation from the blood vessel and heart cavity wall.

When the pacemaker lead has tines lodging the tip to the heart tissue or when the movement of the lead is restricted in a blood vessel, a separator is inserted over the heart lead with the stylet wire secured thereto. The separator is preferably a tube made from a material, such as a TEFLON material, for moving easily over the heart lead and through the blood vessel. The distal end of the tube is beveled and has an edge for separating the heart lead from the blood vessel wall as the tube is moved along a length of the heart lead. A hollow metal tip having a beveled cutting edge is attached to the distal end of the tube to separate a restricted lead encapsulated, for example, by fibrotic tissue. The secured stylet wire advantageously limits movement of the heart lead to facilitate separation and also minimizes damage to the blood vessel as the tube is passed along a length of the heart lead separating the heart lead from the blood vessel wall.

After passing through the blood vessel, the tube is moved to the distal end of the heart lead next to the heart cavity wall for separating the tines at the tip of the lead from the heart tissue without causing injury thereto. The tube is held in place next to the heart cavity wall or pushed just slightly, while the stylet wire is pulled to engage the tip of the heart lead against the beveled distal end of the tube. The tube is then rotated back and forth to cause the tines at the tip of the heart lead to dislodge and separate from the trabeculae and fibrotic tissue that secure the lead to the heart cavity wall. As a result, the tip of the heart lead is advantageously separated from the heart wall without causing injury to the heart tissue.

Another advantage of this lead removal apparatus is when the lead cannot be removed because of some complication. In such case, the separator tube is removed from the blood vessel, and the stylet wire is rotated to unsecure and unscrew the wire coil and the stylet wire from the coiled structure of the heart lead. This advantageously permits the removal of the stylet wire from the coiled structure without having to perform open heart surgery. This represents a significant advantage over the prior art device in which the beveled rod and an actuating wire cannot be removed from the heart lead after the distal end has engaged and deformed the coiled structure. In such instance, open heart surgery is then required to remove the lead.

The invention also includes the method of removing the pacemaker lead implanted in a heart by determining the passageway of the lead with a wire guide and by inserting the distal end of the stylet wire with the wire coil attached thereto into the longitudinal passageway formed by the coiled structure of the lead. A back and forth rotation of the stylet wire is advantageously used to free the stylet wire and wire coil if there is a tendency for the stylet wire to prematurely engage the coiled structure of the heart lead. After the stylet wire is fully inserted, the stylet is rotated a number of times usually in a counterclockwise direction to engage the wire coil with the coiled structure. As a result, the stylet wire is secured to the coiled structure.

The method further includes restricting movement of the coiled structure within the insulating material with a tie secured at the proximal end of the lead. The secured stylet wire is then further rotated to dislodge the tip of the lead from the heart tissue. The dislodged lead is removed from the heart by pulling the secured stylet wire and lead from the heart.

When a blood vessel restricts movement of the lead or the tip of the lead has tines, a separator tube with a metal cutting tip is inserted over the heart lead with the stylet wire secured thereto after the stylet wire is secured to the heart lead. As the separator tube is moved along the length of the heart lead, the stylet wire limits the movement of the heart lead to permit the separation of the heart lead from an encapsulating blood vessel. When fully inserted to the heart lead tip, the separator tube is held in place or pushed slightly, and the stylet wire is pulled to engage the tip of the heart lead with the beveled distal end of the tube. The separator tube is then rotated back and forth to dislodge the tines and separate the tip of the lead from the heart cavity wall without causing any trauma thereto.

Since the coiled structure of the heart lead is commonly wound in a clockwise direction, the stylet wire coil is wrapped around the stylet wire in a counterclockwise direction opposing the direction of the coiled structure. This permits the easy engagement and disengagement of the stylet wire with the heart lead when the stylet wire is rotated in either a counterclockwise or clockwise direction.

In another embodiment of the lead removal apparatus, a lock wire having a plurality of turns about the distal end is attached about the distal end of the stylet wire, and the proximal end is extended beyond the passageway of the lead. The proximal end of the lock wire is secured when the inserted stylet wire is rotated to engage the turns of the lock wire with the coiled structure. The stylet wire and lock wire have a combined diameter for passing through a deformed segment of the coiled structure. The deformed segment usually has a much smaller diameter than the distal end of the lead, and the secured proximal end of the lock wire advantageously permits the turns at the distal end thereof to expand and engage the larger diameter at the distal end of the lead.

DETAILED DESCRIPTION

Figures 1, 3, 4:
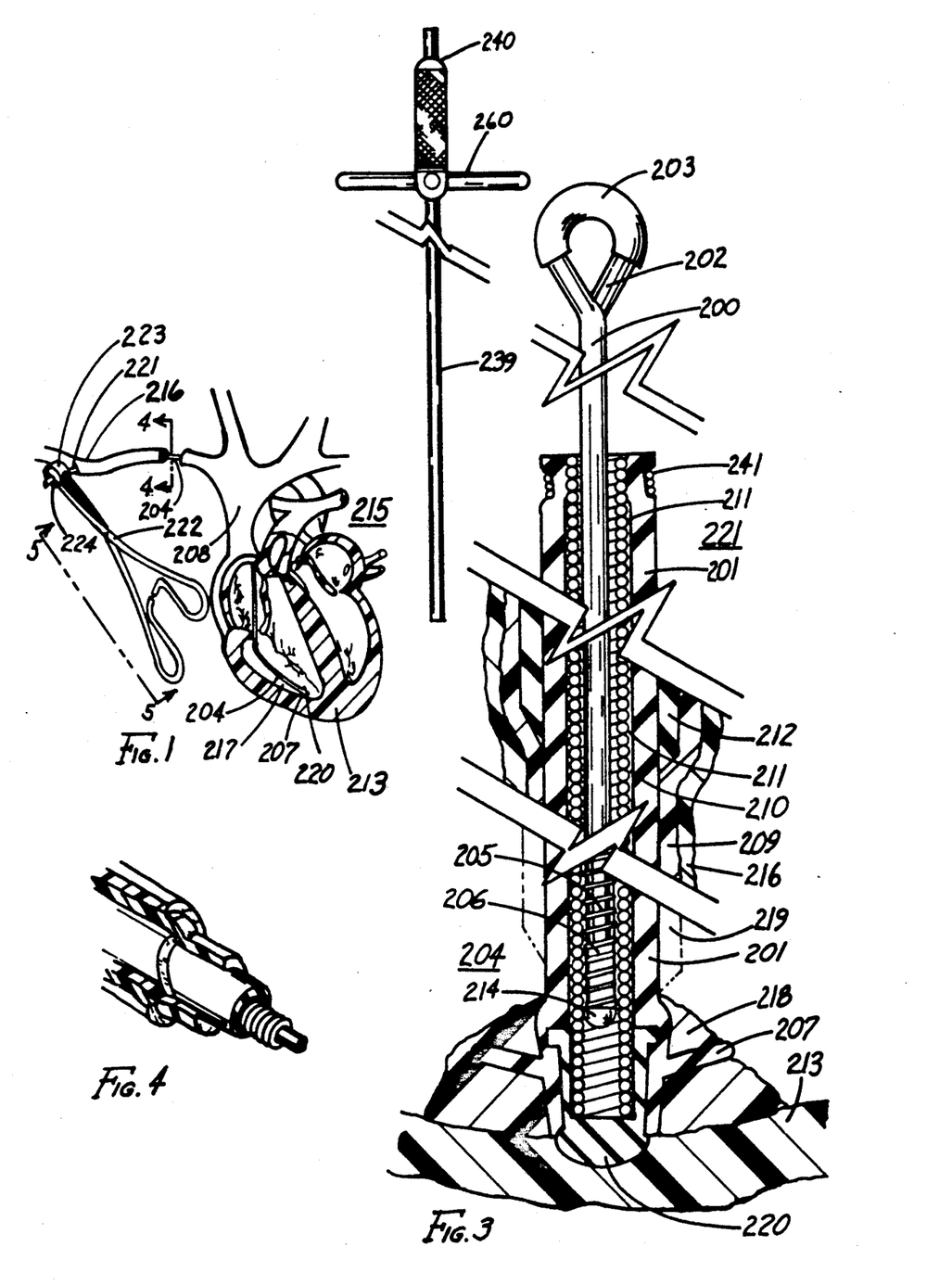
FIG. 1 depicts a partial cross-sectional view of a heart having an electrical pacemaker lead implanted therein.
FIG. 3 illustrates a wire guide and sections of the apparatus of the present invention for separating a length of a heart lead restricted in a blood vessel and for separating the tip of the heart lead from a heart cavity wall.
FIG. 4 illustrates the leading edge of the separator tube of the apparatus of FIG. 3 for separating the heart lead from a blood vessel as partially shown in FIG. 1.

Depicted in FIG. 1 is a partial cross-sectional view of heart 215 connected to a plurality of arteries and veins such as the right subclavian vein 216 through which an electrical heart pacemaker lead 204 has been implanted. The lead passes internally through the right subclavian vein 216, the superior vena cava 208 and into the right ventricle 217 of the heart. The distal end of the lead includes an electrode 220 for electrically stimulating the heart and is secured to the apex of the right ventricle with a plurality of tines 207, which in time become securely attached to the ventricle wall by endothelial tissue forming around the heart lead tip. Some ventricles are relatively smooth on the inside, but most have trabeculae amongst which the tines are secured into position. External to the right subclavian vein, the proximal end 221 of the lead is grasped by a lockable mechanism 222, which will be described hereinafter.

Figure 2:
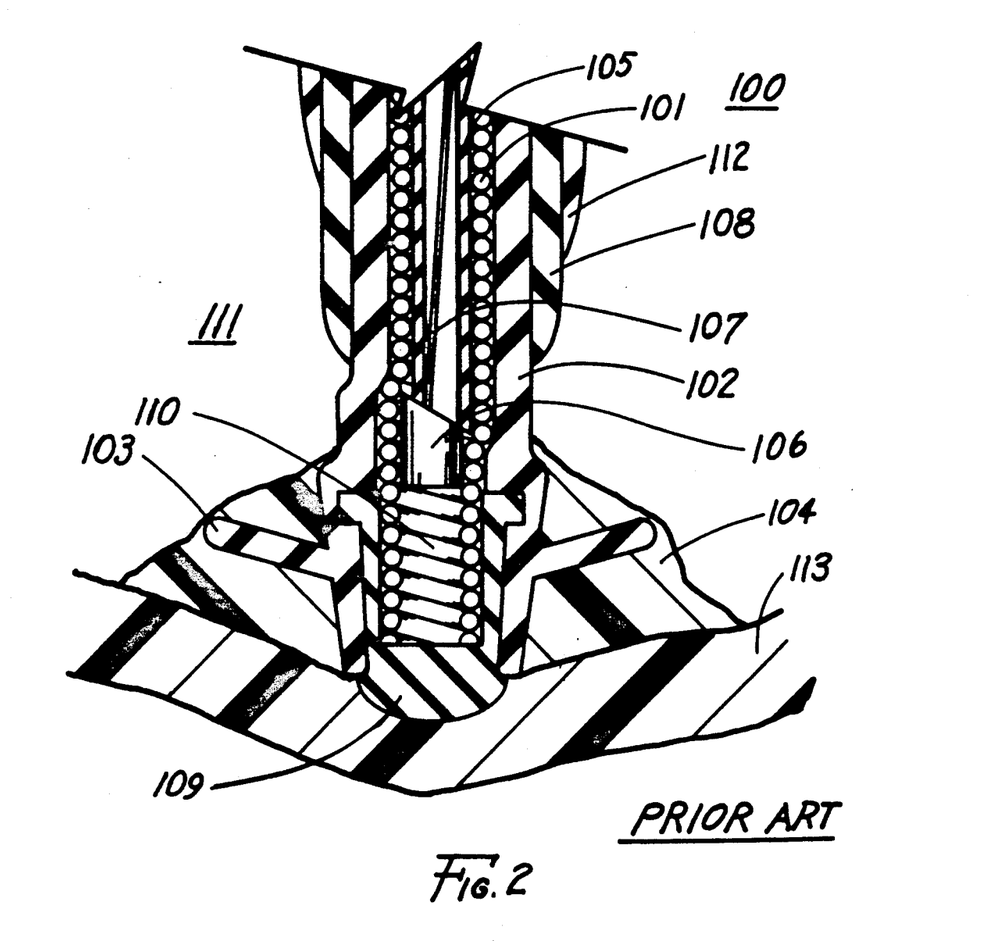
FIG. 2 depicts a partial cross-sectional view of a prior art tool inserted in the passageway of a heart lead for removing the lead.

Depicted in FIG. 2 is a partial cross-sectional view of a prior art tool 100 for removing a heart lead 111 which has been secured to a heart cavity wall 113 via trabeculae and/or fibrotic tissue 104. The lead includes an electrical coiled structure 101 and insulating material 102 that is formed essentially into a tube for covering the outer surface of the coiled structure and for preventing fluids from entering the coiled structure. At the distal end of the heart lead are tines 103, that are formed from the insulating material, for securing the heart lead tip including electrode 109 to the heart cavity wall. Tool 100 includes a hollow rigid tube 105 and beveled rod 106 for inserting in the longitudinal passageway 110 of the heart lead coiled structure. In the passageway of hollow tube 105 is an actuating wire 107 connected to beveled rod 106. The trailing edge of the beveled rod and the leading edge of the hollow tube are inclined at an angle for moving the beveled rod across the distal end of the hollow tube when the actuating wire is pulled. When moved, the beveled rod engages and deforms the heart lead coiled structure as shown. The deformed coiled structure locks the hollow tube and beveled rod in place for limiting movement of the heart lead. However, once secured, beveled rod 106 may not be extracted from passageway 110 of the coiled structure since the deformed coiled structure prevents the beveled rod and actuating wire from traversing the passageway. The prior art tool also includes a hollow dilator 108 for sliding over the heart lead coil and separating the heart lead from the blood vessel. A hollow explanator 112 passes over the dilator and is rotated back and forth to explant the tip of the heart lead from the securing tissue and heart wall.

Depicted in FIG. 3 is a flexible stylet wire 200 of the present lead removal apparatus invention that is insertable in the longitudinal passageway 210 of a heart lead coiled structure 211 for controlling and, in particular, limiting the movement of heart lead 204 including coiled structure 211. Heart lead 204 also includes insulating material 201, such as silicone or polyurethane, formed into a hollow tube that surrounds the coiled structure and prevents fluids from making contact with the coiled structure. Attached to the distal end of the flexible stylet wire is an expandable wire coil 205 consisting of approximately 25 turns of wire with spacing between the turns. Five to seven wraps of the wire coil are attached to the distal end of the stylet wire using, for example, solder 206. The remaining wraps of the wire coil remain free for engaging the coiled structure when the proximal end of the stylet wire is rotated in a direction to unwind and expand the turns of the wire coil and engage the coiled structure of the heart lead. A bead 214 of high temperature silver solder is applied to the distal end of the stylet wire to prevent the distal end thereof from pulling through the wire coil during separation and removal of the heart lead. Positioned about the proximal end of the stylet wire is control mechanism 202 for rotating the stylet wire in either a clockwise or counterclockwise direction or for moving the wire in a longitudinal direction into or out of the passageway. In this embodiment, control mechanism 202 is a loop of wire formed from the stylet wire of which the physician may grasp or insert his finger. The loop may also be fashioned for attachment to another control mechanism for moving the stylet wire. Other control mechanisms such as a slidable chuck may be positioned at the proximal end of the stylet wire to facilitate movement of the stylet wire. The formed loop 202 is covered with a TEFLON material tubing 203 or other suitable material for facilitating the easy movement of the stylet wire. The looped end is also compressible for inserting through a separator tube 212.

The choice of the stylet wire and coil wire varies with the internal diameter of the coiled structure which varies from 0.016" to about 0.028" for most heart leads. The diameter of the stylet wire would then range from 0.009" to 0.015", with the coil wire ranging in diameter from 0.003" to 0.006". The use of stainless steel wire is preferable. The stylet wire should be hardened wire, but ductable wire may be used for the coil wire.

Figures 5, 6:
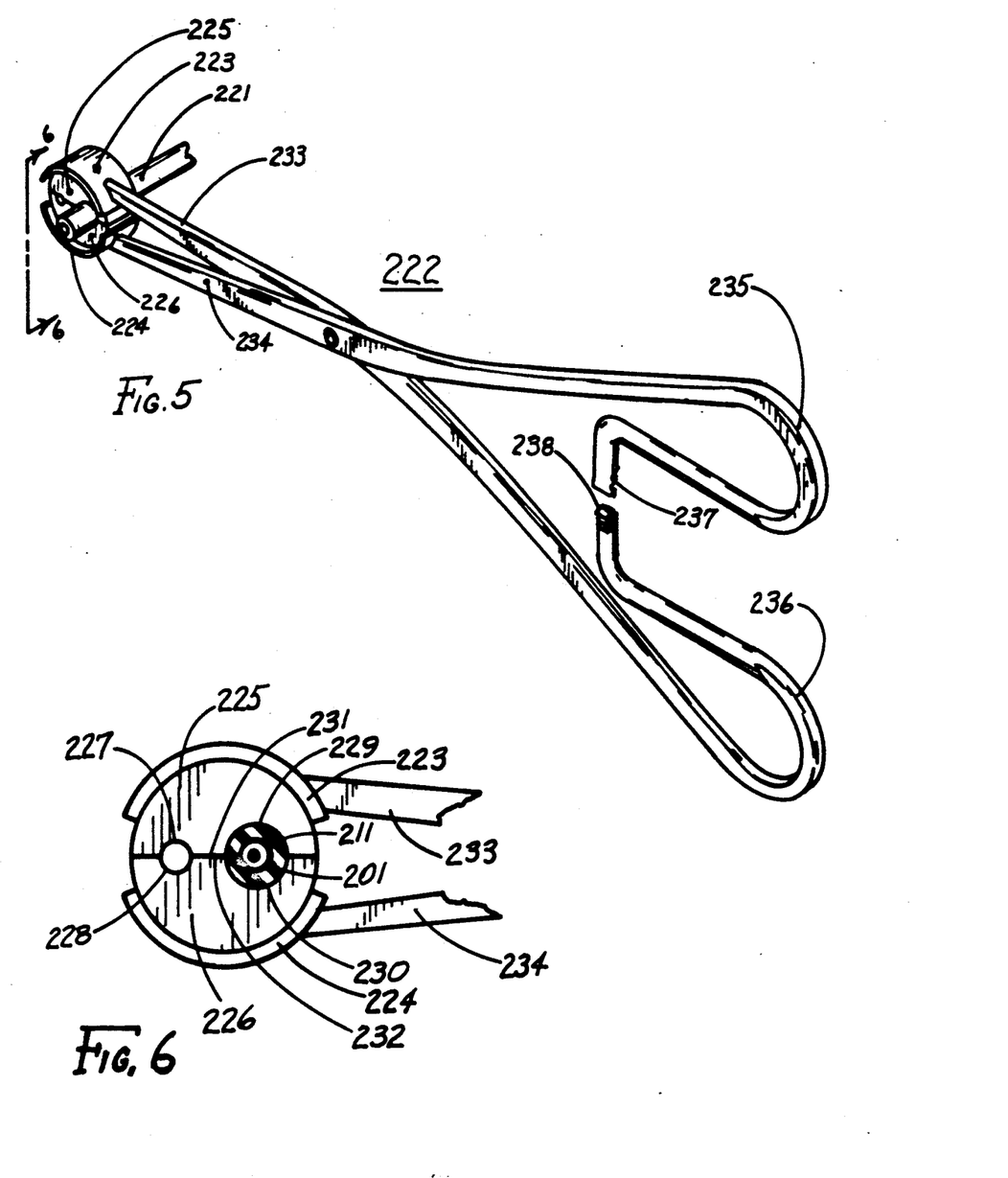
FIG. 5 depicts a lockable mechanism for grasping the proximal end of the pacemaker lead of FIG. 1.
FIG. 6 depicts an enlarged view of the lockable mechanism of FIG. 5 along the lines 6—6.

Before the stylet wire is inserted into passageway 210 of the lead, the inside diameter of the coiled structure and the outside diameter of the insulating material are determined. First, lockable mechanism 222 is first applied to the proximal end 221 of the lead between opposing semicircular jaws 223 and 224. The details of mechanism 222 are depicted in FIGS. 5 and 6. Semicylindrical pliable material 225 and 226, such as latex, are affixed with medical grade adhesive to the opposing faces of the jaws. Semicylindrical pliable material 225 includes semicylindrical channels 227 and 229 having different radii, and pliable material 226 includes semicylindrical channels 228 and 230 with radii corresponding to channels 227 and 229, respectively. When jaws 223 and 224 are in a closed position, the opposing surfaces 231 and 232 of respective pliable material 225 and 226 are in contact with opposing channels 227 and 228 forming one hollow cylindrical passageway with a first diameter and opposing channels 229 and 230 forming a second hollow cylindrical passageway with a second larger diameter. The two different size diameter passageways in the pliable material accommodate a number of different size diameter pacemaker leads and are designed to grasp and apply pressure to insulating material 201 in a uniform manner.

When proximal end 221 of lead 204 is inserted and grasped in the hollow passageway formed by channels 229 and 230, insulating material 201 is compressed onto coiled structure 211, thus limiting the movement of the structure within the insulating material. When the physician cuts the lead for access to the passageway of the lead, the compressed insulating material prevents the coiled structure from retracting into the passageway of the lead.

Pivotly interconnected elongated members 233 and 234 are connected to respective opposing jaws 223 and 224 to operate the jaws between open and closed positions. The proximal ends 235 and 236 of the members are curved as shown in FIG. 5 to oppose each other and have a respective plurality of teeth 237 and 238 that interlock to form a locking mechanism. The locking mechanism is actuated by squeezing the proximal ends of the members and opposingly positioning the teeth thereon. When so positioned, the teeth of mechanism 222 interlock and maintain opposing jaws 223 and 224 in a closed position.

When lockable mechanism 222 is in a closed position with the proximal end of the lead grasped between jaws 223 and 224 and the passageway of the lead exposed, the physician selects a wire guide 239, as shown in FIG. 3, having a diameter less the diameter of the lead passageway. The physician determines the passageway by inserting the wire guide therein and sensing for any blockages. The guide includes a control mechanism such as a knurled cylindrical chuck 240 positionable about the proximal end thereof. The physician grasps the knob to extend the guide into the lead passageway and to rotate the guide back and forth to clear or break through any blockages caused by tissue or occluding material. The guide is also used to determine or size the inside diameter of a second coiled structure that may be coaxially positioned inside coiled structure 211. When utilized as a control mechanism for stylet wire 200, the chuck may also include appendages 260 for rotating and counting the number of times the stylet wire is rotated. Having determined the lead passageway with the wire guide, several other guides similar to guide 239 are individually inserted in the passageway to determine the actual inside diameter at the proximal end. Guide 239 is also utilized to determine if coiled structure 211 has been deformed or damaged and to determine the smallest diameter of the coiled structure and passageway.

As shown in FIG. 3, stylet wire 200 is inserted into longitudinal passageway 210 of coiled structure 211. The diameter of the coil wire and stylet wire have been selected to form a combined overall diameter which approximates the diameter of the longitudinal passageway of the heart lead coiled structure within a predetermined tolerance such as one or two thousandths of an inch. Stylet wire 200 is then fed through the entire length of the passageway to the distal end of the heart lead coiled structure which is secured to the wall of heart cavity tissue 213. When fully inserted into the heart lead, the distal ends of the stylet wire and heart lead coiled structure should be in close proximity. It is not necessary, but probably more advantageous, that the stylet wire be attached to the distal end of the heart lead. For separating the heart lead from adjacent tissue, the stylet wire may be secured anywhere along the passageway of the coiled structure past the restricting tissue. To secure the stylet wire to coiled structure 211, looped end 202 of the stylet wire is operated in a circular direction to unwind and expand wire coil 205. As a result, the turns of the wire coil and coiled structure engage and intermesh, thereby firmly securing the stylet wire to the heart lead. This prevents any extension or stretching of the heart lead and also controls and limits the movement of the lead when separator tube 212 is moved along the length of coiled structure 211 and insulating material 201 of the heart lead.

After the stylet wire is secured to the lead and prior to inserting separator tube 212 over the stylet wire and lead, a tie 241 of, for example, nylon cord or suture material is wrapped around proximal end 221 of the lead to secure insulating material 201 to coiled structure 211. The tie controls or limits the movement of the coiled structure within the insulating material. With the insulating material secured to the coiled structure at the proximal end, removal force is applied not only to the coiled structure, but also to the insulating material of the lead as well. This maintains the integrity of the heart lead during subsequent tissue separation from the insulating material. In those instances where the stylet wire has not been fully inserted to the distal end of the lead, the tie also prevents the coiled structure from unravelling, breaking or separating from electrode 220 or the rest of the lead.

As previously suggested, the looped proximal end of the stylet wire can be compressed to permit separator tube 212 to be inserted thereover and over the insulating material of the heart lead. Separator tube 212 comprises a semi-rigid material, such as a TEFLON material for sliding easily through the blood vessel and over the insulating material of the heart lead. In order to place the separator tube over the stylet, the stylet should extend at least 12 inches beyond the person's body so that the looped end can be grasped to apply tension to the stylet. With the separator tube 10 to 12 inches long, the stylet is typically three feet long.

Depicted in FIG. 4 is fibrotic tissue 209 encapsulating heart lead 204 in blood vessel 216. When this occurs in small diameter veins where blood flow has been restricted or prevented, separation and removal of the lead from the tissue is difficult and often causes severe damage or destruction to the vein. Without tension on stylet wire 200, separation is usually not possible in these situations.

Figures 7, 8:
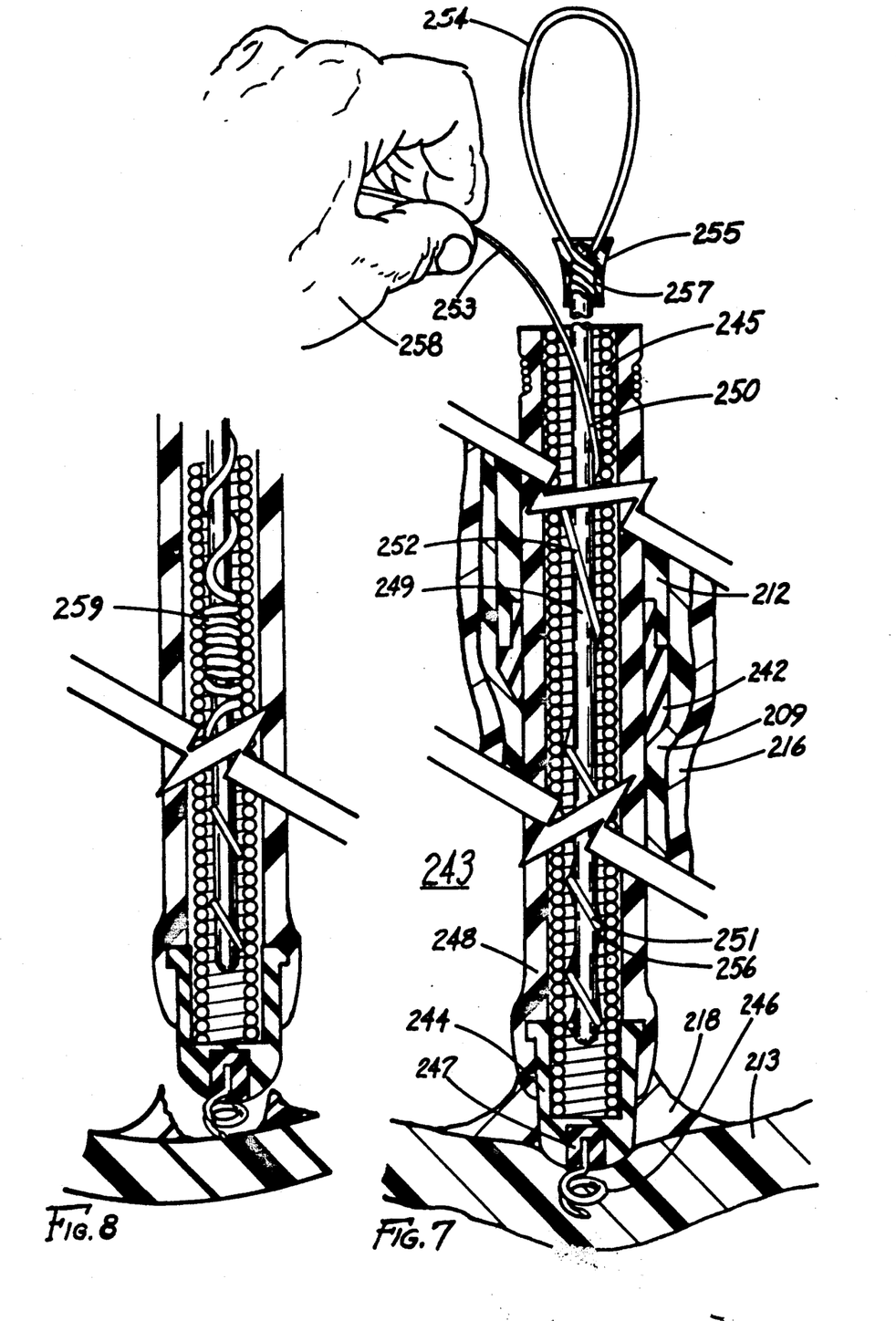
FIG. 7 depicts another embodiment of the lead removal apparatus of this invention.
FIG. 8 depicts the lead removal apparatus of FIG. 7 with the stylet wire secured to the pacemaker lead.

As shown, the distal end of the separator tube 212 is beveled and includes a cutting edge or edge having a number of teeth for separating heart lead insulating material 201 from encapsulating fibrotic tissue 209. As depicted in FIG. 7, hollow separator tube 212 has a metal beveled tip 242 attached to the distal end thereof with, for example, a medical grade adhesive. The metal tip provides a more durable edge for separating or cutting encapsulating fibrotic tissue from the lead.

Returning the reader's attention to FIG. 3, separator tube 212 is moved and rotated along the outer surface of insulating material 201 of the heart lead to separate the lead from the blood vessel wall. After the separator tube has been moved along the entire length of the heart lead, it will abut next to the heart cavity wall as shown by phantom lines 219. The distal end of the heart lead is typically secured to the heart cavity wall by trabeculae or fibrotic tissue 218 that has encapsulated tines 207 positioned at the distal end of the lead. The separator tube 212 is positioned next to the heart cavity wall or pushed slightly while the stylet wire is tensioned in the opposite direction. The separator tube is then rotated back and forth to dislodge and separate tines 207 and the distal end of the heart lead from fibrotic tissue 218 and heart cavity wall 213. As a result, the heart lead has now been completely separated from the blood vessel and the heart cavity wall for subsequent removal. The separator tube, the stylet wire, and the heart lead are then removed from the heart cavity and surrounding blood vessel.

However, should the removal of the heart lead be prevented for whatever reason, the stylet wire is rotated in a clockwise direction to unsecure the stylet and wire coil from the heart lead coiled structure. The time for this operation is lessened by attaching a rotating mechanism such as an electrical screwdriver to the proximal end of the stylet wire.

Depicted in FIG. 7 is another illustrative embodiment of the lead removal apparatus of this invention. In this embodiment, pacemaker lead 243 is similar to the lead shown in FIG. 3; however, the distal end of the lead is of a different configuration. In particular, electrode 244 has two cavities therein. One cavity is for receiving the coiled structure 245 of the lead. The second cavity is for receiving and securing anchoring coil 246 secured in the cavity with insulating material 247 in a well-known manner. The distal end of anchoring coil 246 is cut to form a beveled or sharpened edge for turning or corkscrewing the coil into heart cavity wall 213. Anchoring coil 246, as a result, securely attaches electrode 244 to the heart tissue to establish good electrical contact for stimulating the heart tissue with electrical pacing pulses from the pacemaker. Insulating material 248 surrounds coiled structure 245 and partially surrounds electrode 244. Since anchoring coil 246 is utilized in this configuration, the insulating material is molded over the coiled structure and electrode without forming tines for the endothelial tissue to form therearound.

Stylet wire 249 of this lead removal apparatus and lock wire 250 attached to the distal end thereof have a combined diameter much less than the inside diameter of coil structure 245 of the lead. This is particularly advantageous for those situations when the coiled structure of the lead has been deformed, unraveled, or in some way damaged. In this embodiment, lock wire 250 has a plurality of turns 251 wrapped around the distal end of the stylet wire. Turns 251 of the lock wire at the distal end of the stylet wire are closely wrapped and attached to the distal end of the stylet wire using, for example, a silver solder. Turns 252 of the lock wire are more loosely wrapped and are approximately 75 in number. The unwrapped proximal end 253 of the lock wire extends beyond the passageway of the lead and is secured and positioned by, for example, the physician's hand 258 when the stylet wire is rotated to expand lock wire turns 252 and engage the turns of coiled structure 245.

Control mechanism 254 such as a loop of malleable wire is wrapped around and secured to the proximal end of the stylet wire using, for example, silver solder 257. Slidable chuck 240 is also suitable for use as the control mechanism for stylet wire 249. A TEFLON material coating 255 surrounds the interconnection to prevent possible injury to the physician or patient. Control loop 254 is provided for the physician to move the stylet wire in and out of the passageway of the lead as well as rotate the stylet wire to engage the coiled structure of the lead. When the stylet wire is secured to the pacemaker lead, loop 254 is used to extract stylet wire and pacemaker lead from the patient.

To unravel the turns of the lock wire, a tool such as an electrical screwdriver is attached to the control mechanism loop to rotate the stylet wire and expand the turns of the lock wire. While the stylet wire is being rotated, the physician secures the position of the proximal end 253 of the lock wire to permit lock wire turns 252 to tangle and form a bundle 259 that engages the coiled structure as depicted in FIG. 8. The stylet may have to rotate 50 to 100 turns to form bundle 259 and engage coiled structure 245.

After the lock wire has secured the stylet wire to the pacemaker lead, the physician grasps control loop 254 and continues to rotate the stylet wire and pacemaker lead to dislodge anchoring coil 246 from the heart tissue. Should the blood vessels encapsulate the pacemaker lead, separator tube 212 is inserted over the stylet wire and pacemaker lead as previously described to separate the lead from the encapsulating blood vessel tissue. The separator tube may also be extended to the distal end of the pacemaker lead to turn and dislodge the distal end of the pacemaker lead from the heart tissue.

Of course, it will be understood that the aforementioned lead removal apparatus and method is merely illustrative of the application of the principles of this invention and that numerous other arrangements may be devised by those skilled in the art without departing from the spirit and scope of the invention. In particular, a number of other control mechanisms may be attached to the proximal end of the stylet wire for operating the stylet wire in either a clockwise or counterclockwise direction as well as moving the wire longitudinally. Furthermore, this apparatus may be utilized for removing electrical leads from body ducts and passages as well as body tissue that has encapsulated the lead and restricted its movement.

What is claimed is:

1. Apparatus for removing a pacemaker lead implanted in a heart, comprising:
    stylet means for inserting into a longitudinal passageway of said implanted lead; and
    coil means attached about a distal end of said stylet means for radially expanding about said stylet means and securing said stylet means to said lead when said stylet means is inserted in said passageway.

2. The apparatus of claim 1 further comprising control means positioned about a proximal end of said stylet means for rotating said coil means to engage said lead.

3. The apparatus of claim 1 further comprising control means positioned about a proximal end of said stylet means for controlling movement of said stylet means.

4. The apparatus of claim 1 further comprising control means positioned about a proximal end of said stylet means for removing said implanted lead from said heart when said stylet means is secured to said implanted lead.

5. The apparatus of claim 1 further comprising tie means for securing a proximal end of said pacemaker lead to said stylet means when said distal end of said stylet means is secured to said pacemaker lead.

6. The apparatus of claim 1 further comprising tie means for securing about insulating material and a coiled structure of said lead after said distal end of said stylet means is secured to said coiled structure.

7. The apparatus of claim 1 further comprising guide means insertable into said passageway for determining a size of said passageway.

8. The apparatus of claim 1 further comprising separator means positionable about a length of said implanted lead for separating said lead from biological tissue restricting movement of said lead when said stylet means is secured to said pacemaker lead.

9. The apparatus of claim 8 wherein said separator means includes a tube and tip means positioned about a distal end of said tube and formed for separating said lead and said tissue.

10. The apparatus of claim 1 further comprising lockable means for grasping a proximal end of said lead.

11. The apparatus of claim 10 further comprising:
first and second opposing means for grasping said lead therebetween in a closed position;
first and second elongated means each having a distal end connected to an individual one of said first and second opposing means, respectively, and pivotly interconnected for operating said opposing means between an open and said closed position; and
pliable material means affixed to each of said opposing means for grasping said lead therebetween without deforming said lead.

12. The apparatus of claim 11 further comprising locking means having first and second portions each positioned about an individual proximal end of said elongated means for locking said opposing means in said closed position when said locking means is locked.

13. The apparatus of claim 11 wherein said pliable material means affixed to each of said opposing means has channel means formed therein for grasping said lead and applying pressure thereto in a uniform manner.

14. Apparatus for grasping a pacemaker lead and limiting movement of a coiled structure within a surrounding insulating material of said lead, comprising:
first and second opposing jaws for grasping said lead therebetween in a closed position;
first and second elongated members each having a distal end connected to an individual one of said first and second jaws, respectively, and pivotally interconnected for operating said jaws between an open and said closed position; and
pliable material affixed to each of said opposing jaws and each having semi-circular channel means formed therein for applying pressure to said lead in a uniform manner.

15. The apparatus of claim 14 further comprising a locking mechanism having a first and second portions each positioned about an individual proximal end of said members for locking said jaws in said closed position when said locking mechanism is actuated.

16. A method for removing a pacemaker lead implanted in a heart, comprising the steps of:
determining a size of a longitudinal passageway of said lead;
inserting a stylet wire in said longitudinal passageway;
securing said stylet wire to said pacemaker lead with a wire coil attached about a distal end of said stylet wire; and
removing said lead from said heart.

17. The method of claim 16 further comprising dislodging a distal end of said lead and pulling said stylet wire to remove said lead from said heart when said distal end of said lead is dislodged from said heart tissue.

18. The method of claim 14 further comprising separating said lead from tissue with a separator when said stylet wire is secured to said lead.

19. The method of claim 18 wherein said separating comprises inserting said separator over said lead when secured to said stylet wire and moving a distal end of said separator along a length of said lead restricted in said tissue.

20. The method of claim 16 further comprising securing a wire extending from said wire coil and said passageway.

21. The method of claim 16 further comprising restricting movement about a proximal end of a coiled structure within a insulating material of said lead with a tie after said stylet wire has been inserted in said lead.

22. The method claim 16 further comprising rotating said stylet wire when secured to said pacemaker lead to dislodge a distal end of said pacemaker lead lodged in tissue of said heart.

23. The method of claim 16 further comprising:
inserting a tube over said lead to said distal end thereof when said stylet wire is secured to said lead;
engaging a distal end of said tube against said distal end of said lead lodged in tissue of said heart; and
rotating said tube to dislodge said distal end of said lead from said heart tissue.

24. Apparatus for removing a pacemaker lead implanted in a heart, comprising:
stylet means for inserting into a longitudinal passageway of said implanted lead; and
lock wire means having a distal end, a proximal end and a plurality of turns wrapped about a distal end of said stylet means, said distal ends of said lock wire means and said stylet means being attached together, said proximal end of said lock wire means extending beyond said passageway of said lead when said stylet means is inserted therein, said lock wire means for securing said stylet means to said pacemaker lead when said proximal end of said lock wire means is secured beyond said passageway and said stylet means is rotated to unwrap said turns.

* * * * *